(12) United States Patent
Rose et al.

(10) Patent No.: US 6,288,010 B1
(45) Date of Patent: Sep. 11, 2001

(54) COMPOSITIONS COMPRISING ANTI-DRIFT AGENTS AND PROCESSES AND METHODS FOR THEIR USE

(75) Inventors: Simon Alexander Hanson Rose; Jayne Anne Snowden, both of West Yorkshire (GB)

(73) Assignee: Ciba Specialty Chemicals Water Treatments Limited, Bradford (GB)

( * ) Notice: Subject to any disclaimer, the term of this patent is extended or adjusted under 35 U.S.C. 154(b) by 0 days.

(21) Appl. No.: 09/428,100

(22) Filed: Oct. 27, 1999

(30) Foreign Application Priority Data

Oct. 30, 1998 (DE) .................................................. 9823752

(51) Int. Cl.⁷ .................................................. A01N 25/30
(52) U.S. Cl. .......................... 504/206; 504/362; 514/975
(58) Field of Search ................................. 504/206, 362; 71/33, 34, 59, 64.1; 514/975

(56) References Cited

U.S. PATENT DOCUMENTS

| | | | |
|---|---|---|---|
| 3,360,356 | 12/1967 | Vartiak | 71/65 |
| 5,525,575 | 6/1996 | Chamberlain | 504/116 |
| 5,529,975 | 6/1996 | Chamberlain | 504/116 |
| 5,550,224 | 8/1996 | Hazen | 536/114 |

FOREIGN PATENT DOCUMENTS 2 107 986  5/1983 (GB).

91/14365  10/1991 (WO).

OTHER PUBLICATIONS

Turner, D. J. "Effects on glyphosate performance of formulation, additives and mixing with other herbicides". Chapter 15 in The Herbicide Glyphossate. Grossbard et al, ed. p. 221–240, 1985.*

* cited by examiner

Primary Examiner—S. Mark Clardy
(74) Attorney, Agent, or Firm—David R. Crichton

(57) ABSTRACT

A composition (1) comprising water, in solution,
  a) an inorganic water-soluble compound in an amount of at least 10%,
  b) an anti-drift agent which is a water soluble anionic polymer of intrinsic viscosity at least 6 dl/g which is formed from water soluble monomer or monomer blend,
characterized in that the water-soluble polymer (b) is present in an amount up to 1.9 wt. % based on weight of composition.

Said composition (1) can be a liquid fertilizer concentrate that can conveniently be applied through conventional spray distribution equipment without the need for additional dosing of anti-drift control chemicals. Said composition (1) can be a low viscosity liquid anti-drift agent that can be combined with a herbicide or pesticide in conventional spray distribution equipment.

13 Claims, No Drawings

COMPOSITIONS COMPRISING ANTI-DRIFT AGENTS AND PROCESSES AND METHODS FOR THEIR USE

This invention relates to novel aqueous compositions that comprise anti-drift agents and inorganic water-soluble compounds, which can conveniently be applied using conventional spray distribution equipment. The invention also relates to processes of spraying fertilisers, herbicides and pesticides in which the novel compositions are used and methods of reducing spray drift during the spraying process.

It is well known in agriculture to apply various agrochemicals to growing areas by spraying. The growing areas may be crop areas, which can be very large, or smaller growing areas such as those in greenhouses. The agrochemicals applied as sprays include fertilisers, herbicides and pesticides.

Fertilisers can be supplied in various forms, in particular as solid compositions, or as suspensions or solutions of the fertiliser in a liquid. Fertiliser solutions are generally supplied by the manufacturer as an aqueous concentrate in large batches of size around 1 ton in weight. The solutions contain high concentrations, often 10 to 80 wt. % (dry solids), of dissolved inorganic fertiliser.

Herbicides and pesticides can be supplied to the farmer in various forms, for instance as neat liquids, aqueous solutions, aqueous dispersions or slurries of solid herbicide or pesticide. It is normal practice for the manufacturer to supply the farmer with the herbicide or pesticide in the form of a neat liquid or as a high activity solution or slurry. The usual way of applying herbicides or pesticides to an area of land would be by spraying.

Various systems have been devised for convenient dosing of fertilisers, herbicides or pesticides. Spray pumps are well known which spray water from a spray manifold onto the area of land or crop area and which are designed so that concentrated fertiliser solution, herbicide or pesticide can be dosed into the pump, mixed with water before being sprayed.

For some applications it is usual to combine two or more agrochemicals. For instance in the application of herbicides, especially systemic herbicides, it is usual to combine the treatment with a fertiliser, such as for instance ammonium sulphate. The fertiliser stimulates the growth of unwanted plants causing them to take up much more water, together with the herbicide, through the root system. This ensures a more efficient uptake and distribution of herbicide throughout the plant. In this instance the fertiliser may be regarded as an adjuvant in that it increases the efficacy of the herbicide. Thus a fertiliser used in combination with a herbicide is termed a herbicide adjuvant.

During the spraying of fertilisers, herbicides and pesticides it is usual to apply anti-drift agents in order to prevent the formation of fine droplets which could be carried beyond the area intended to be treated. Without the use of anti-drift agents, the spraying of fertilisers, herbicides and pesticides would be inefficient, first of all because there could be inadequate treatment of the land and crop areas intended to be treated and secondly the extraneous spray, if carried beyond the intended treatment zone, could for example be detrimental to other crops, land and water courses.

It is usual to combine the anti-drift agent with either the water which is fed into the spray pumps or to apply it directly into the spray pumps, usually at or shortly after the mixing zone where the water is mixed with the herbicide, pesticide or aqueous fertiliser concentrate. It is important that the spray drift chemical is metered at the correct dose to ensure that extraneous spray is not formed through under dosing or through overdosing the spray angle is too narrow resulting in uneven distribution of the pesticide, herbicide or fertiliser.

Polymers of acrylamide and other ethylenically unsaturated monomers have been used as anti-drift agents. It has been generally accepted that polymers which give optimum spray drift control are either non-ionic (eg acrylamide homopolymer) or have relatively low anionic content (e.g. 5 to 30 wt. %) and also have relatively high intrinsic viscosity, for instance above 6 dl/g. Such polymers tend to form viscous aqueous solutions unless used at low concentration. Normal practice is to mix the polymer powder or reverse phase emulsion form with water directly into the spray tank so as to form an aqueous solution of polymer. However, this has the problem that emulsion polymers can be difficult to activate in this situation and polymer powders take a long time to dissolve. It is sometimes necessary to use more polymer as a result of inefficient dissolution of the polymer. Normally in order to minimise the problems with dissolution it would be usual to use polymers of intrinsic viscosity in the range 6 to 15 dl/g. Typically the water containing the pesticide, herbicide or fertiliser would comprise polymer at a concentration in excess of 0.05 wt. %.

It would be desirable to provide a combined fertiliser composition comprising anti-drift agents that can conveniently be applied through conventional spray distribution equipment without the need for separate dosing of anti-drift control chemicals. It would also be desirable to provide a means for reducing spray drift during the spraying of herbicides or pesticides by conveniently applying a low viscosity, high activity liquid anti-drift control composition.

One aspect of the invention relates to an aqueous composition comprising water, in solution,
 a) an inorganic water-soluble compound in an amount of at least 10% by weight,
 b) an anti-drift agent which is a water soluble anionic polymer of intrinsic viscosity at least 6 dl/g which is formed from water soluble monomer or monomer blend,
characterised in that the polymer (b) is present in an amount up to 1.9 wt. % based on weight of composition.

In a preferred embodiment of the invention the inorganic water-soluble compound is used as a fertiliser. Thus this aspect of the invention relates to a single pack product which provides a combined fertiliser with anti-drift agent that can conveniently be applied through conventional spray distribution equipment and negates separate dosing of additional anti-drift control chemicals. It can be produced by adding polymer (b) to a standard concentrated solution of an inorganic water-soluble salt which is a fertiliser. The amount of polymer used is sufficient to minimise spray drift after dilution of the concentrated solution in the standard manner for fertiliser solutions.

In another aspect of the invention the inorganic water-soluble compound is used as a herbicide adjuvant. The composition of this aspect of the invention enhances the activity of a herbicide with improved anti-drift properties and can be conveniently applied through conventional spray distribution equipment. It can be produced by adding polymer (b) to a standard concentrated solution of an inorganic water-soluble salt which is a herbicide adjuvant, at a concentration that will minimise spray drift after dilution of the concentrated solution in the standard manner for herbicide adjuvant solutions.

It has surprisingly been found that effective spray drift control when spraying pesticide, herbicide or fertiliser can be provided using concentrations of anionic water soluble polymer up to 0.065% based on total weight of dilute aqueous pesticide, herbicide or fertiliser being sprayed, using the aqueous composition comprising at least 10 wt. % inorganic water-soluble salt and up to 1.9 wt. % of an anionic water soluble polymer of intrinsic viscosity of at least 6 dl/g. Furthermore, effective drift control can be achieved by using the water soluble anionic polymers at concentrations of below 0.025%, often below 0.01%, for instance in the range 0.001% to 0.0095%, especially in the range 0.0025% to 0.0075%, based on total weight of dilute aqueous pesticide, herbicide or fertiliser being sprayed.

It has also surprisingly been found that spray drift control is less dose sensitive when using the aqueous composition of the invention. Provided that the minimum amount of anti-drift agent is used, a much wider range of doses will achieve adequate spray-drift control without suffering the effects of overdosing. This is of significant benefit to the farmer in that it ensures a more effective treatment of a crop area or an area of land. By contrast conventional methods of applying anti-drift agents are much more dose sensitive and in order to ensure no risk of spray drift there can be a tendency to overdose, which would result in a narrower spray angle and the consequential inefficient distribution of pesticides, herbicides and fertilisers.

The invention provides an aqueous composition in which the defined polymer (b) is preferably substantially dissolved. That is, the polymer is taken into the solution such that substantially no visible solid material remains.

The polymer must be substantially water soluble and in particular is soluble in the aqueous solution of inorganic water-soluble salt having the same concentration of inorganic water-soluble salt as the aqueous composition which is desired to be produced. Generally the polymer is substantially linear and is not cross-linked.

The polymer has intrinsic viscosity at least 6 dl/g. In this specification intrinsic viscosity is measured by suspended level viscometer at 20° C. in 1 M sodium chloride buffered to pH 7. That is of sufficiently high molecular weight to give spray drift control properties and is not a low molecular weight material which would act as a dispersant.

Preferably IV is at least 8 dl/g, more preferably at least 9 dl/g. It may be up to for instance 30 dl/g but generally it is found that the optimum combination of low viscosity of the composition and spray drift control performance is given by polymers having IV not more than about 20 or 18 dl/g. Preferably IV is not more than 16, more preferably not more than 15 dl/g. Particularly preferred IV ranges are from 9 to 13 dl/g, especially 10 to 12 dl/g.

The polymer is formed from water soluble monomer or monomer blend, usually water soluble ethylenically unsaturated monomer. The anionic content i.e. the proportion of anionic monomer in the monomer blend used to form the polymer, is at least 15 wt. %. It can be up to 100 wt. %, but is preferably not more than 80 wt. %, more preferably not more than 70 wt. %, most preferably not more than 60 wt. %. Particularly preferred polymers have anionic content in the range 20 to 50 wt. %, more preferably in the range 25 to 30 wt. %.

The monomer or monomer blend used to form the polymer comprises any suitable anionic ethylenically unsaturated monomer. It can be a sulphonic monomer, often as sodium or other alkali metal salt, for instance 2-acrylamido-2-methylpropane sulphonic acid. It is generally preferred that the anionic monomer is an ethylenically unsaturated carboxylic monomer, in particular acrylic or methacrylic monomer. Salts of acrylic acid are preferred, for instance ammonium or alkali metal, in particular sodium salts.

The polymer may contain small amounts of cationic monomer, for instance up to 20 wt. % or 10 wt. % but usually the content of cationic monomer is substantially zero.

Generally the anionic monomer is copolymerised with nonionic monomer, usually ethylenically unsaturated water soluble non-ionic monomer such as acrylamide or methacrylamide, preferably acrylamide. Particularly preferred polymers are copolymers of acrylamide with sodium acrylate.

The polymer is included in the composition in an amount such that when the composition is diluted for spraying, it provides adequate spray drift control performance. Polymer concentration in the aqueous fertiliser composition is generally up to 1.9 wt. %, for instance below 1.0 wt. %, preferably below 0.5 wt. %, more preferably below 0.2 wt. %, more preferably below 0.15 wt. %. Particularly preferred compositions comprise polymer concentrations in the range 0.05 wt. % to 0.1 wt. %.

The aqueous composition of the invention can be made in any convenient manner. For instance polymer may be added to water followed by fertiliser or the two may be added simultaneously. Alternatively, fertiliser may be added to a preformed solution of polymer. However, generally it is preferred that polymer is added in solid form, ie powder or bead. It is possible to add it in other forms, such as reverse phase dispersion, but solid is preferred. Preferred solids are in the size range 70 to 2,000 microns and are made in a standard manner, for instance by suspension polymerisation to provide polymer in bead form or by solution polymerisation, followed by comminution and drying, to provide polymer in powder form.

Thus the invention relates to a process for the production of an aqueous composition of the invention comprising providing a preformed aqueous solution of the fertiliser (a) and mixing into it polymer (b) in powder form.

The thus formed composition should have viscosity which renders the composition easy to handle. It should in particular be easy to handle (i.e. preferably pumpable, pourable or sprayable) in the equipment which is presently used for spraying. The polymer may be added to the fertiliser at the facility of the fertiliser manufacturer and thus the viscosity should be low enough that the resulting solution can be handled by equipment presently in place in such facilities. Preferably viscosity is below 3,000 cPs, more preferably not more than 1,000 cPs. In particular it is not more than 500 and especially not more than 250 cPs. Particularly preferably it is not more than 100 cPs. Usually it is in the range of 5 to 50 cPs, preferably 10 to 30 cPs, more preferably in the range 15 to 20 cPs. In this specification viscosity is measured using a Brookfield LVT viscometer using spindle 4 at 30 rpm.

Thus aqueous composition of the invention may be sprayed directly onto an area of land or especially a crop. However, the composition of the invention is intended particularly as a concentrate for use in diluted compositions to be sprayed.

Prior to spraying, the aqueous composition of the invention will be diluted with water and optionally additional agricultural chemical will be added. Typically the aqueous composition of the invention is diluted to a concentration of below 10 wt. % based on total weight of dilute product to be sprayed. Preferably the composition of the invention is diluted to between 1 and 5 wt. %, more preferably 2 to 3 wt. %, most preferably about 2.5 wt. %.

The composition comprises an inorganic water-soluble compound in solution. The inorganic water soluble compound is preferably a fertiliser or herbicide adjuvant. In many instances fertilisers and herbicide adjuvants would be the same selection of compounds. The fertiliser or herbicide adjuvant is present at a concentration of at least 10 wt. % and is usually as high as is convenient, for instance at least 20 wt %. Preferably it is at least 30 wt. %. It can be as high as 70 or 80 wt % but is usually not more than 60 wt. %. Preferred concentration ranges are 30 or 40 to 55 wt. % for instance around 50 wt %.

Urea and any of the known inorganic fertiliser materials can be used, which provide nitrogen, phosphorus and/or potassium either alone or in mixture. These contain ionic salts and include ammonium nitrate, ammonium sulphate, mono ammonium phosphate, diammonium phosphate, mono potasssium phosphate, dipotassium phosphate, polyphosphate salts, potassium chloride, potassium sulphate and calcium nitrate. A particularly preferred fertiliser and herbicide adjuvant is ammonium sulphate.

Examples include urea/ammonium nitrate (32-0-0), potassium chloride (0-0-10), ammonium sulphate (8-0-0-9S), a blend of calcium and ammonium nitrate, and blended fertilisers with the following analyses: 19-0-8, 10-0-10, 3-18-18,0-0-25-17S, 10-10-10 and 14-2-10-2+2.5% organic matter (OM).

The fertiliser composition of this invention may also be used in combination with one or more other agricultural chemicals, for instance herbicides or pesticides, especially systemic herbicides, such as glyphosate or glufosinate. A particularly preferred composition for spraying comprises ammonium sulphate and glyphosate. The additional agricultural chemical(s) would generally be combined with the fertiliser composition during the spraying process. They may be applied as a separate feed into the dilution water or directly into the spray equipment. For instance the additional agricultural chemical may be combined with the fertiliser slightly ahead of or directly into the mixing zone within the spray distribution equipment.

The invention is particularly useful when it is known to be desired to apply a particular fertiliser by spraying and where the spraying would be facilitated by not requiring a separate dosing of anti-drift agent. It is of additional value when the fertiliser composition is used in combination with other agricultural chemicals, for instance herbicides and pesticides.

Preferably the aqueous fertiliser composition of the invention is an aqueous fertiliser concentrate. Prior to spraying, the aqueous fertiliser concentrate of the invention will be diluted with water. Typically the concentrate can be diluted to a concentration of below 10 wt. % based on total weight of dilute product to be sprayed. Preferably the aqueous fertiliser concentrate is diluted to between 1 and 5 wt. %, more preferably 2 to 3 wt. %, most preferably about 2.5 wt. %.

The optimum polymers may vary according to the specific inorganic water-soluble compound or combination of inorganic water-soluble compound with additional agricultural chemical.

In general polymers of anionic content of at least 15 wt. % are more soluble in the solution of inorganic water-soluble salt, and are thus more effective as anti-drift agents in this invention. Preferably the anionic polymers used in the composition of this invention have an anionic content in the range 15 to 50 wt. % especially 25 to 30 wt. %.

Desirably the aqueous composition may comprises at least 10 wt. % ammonium sulphate in solution together with up to 1.9 wt. % water soluble anionic polymer of intrinsic viscosity between 8 and 30 dl/g and an anionic content of above 15 wt. %. Preferably the water soluble anionic polymer has an intrinsic viscosity between 8 and 20 dl/g and an anionic content of above 15 wt. %. Preferably the concentration of ammonium sulphate is at least 30 wt. %. More preferably the polymer has an intrinsic viscosity between 10 and 15 dl/g. Typically the anionic polymer is present in an amount below 1.0 wt. % based on total weight of composition, preferably below 0.5 wt. %. Particularly preferred is a composition in which the anionic water soluble polymer is present in an amount below 0.2 wt. % based on weight of composition, preferably below 0.15 wt. %. More preferred is a composition where the concentration of anionic polymer is present in an amount between 0.05 wt. % and 0.1 wt. % based on total weight of composition. Typically the composition would comprise an anionic polymer of which the anionic content is between 20 and 50 wt. %, preferably 25 to 30 wt. %, based on total weight of composition. Most preferred would be a composition comprising a copolymer of acrylamide with acrylic acid, or alkali metal or ammonium salt thereof. Preferably the composition is prepared by adding solid anionic polymer to a solution of ammonium sulphate solution.

Another advantage of the present invention is that the efficacy of herbicides, especially systemic herbicides, for instance as glyphosate or glufosinate has surprisingly been found to be synergistically enhanced, when used in the composition of the present invention. It is believed that the a water soluble anionic polymer may be acting as an adjuvant. This improvement in efficacy has been observed for various anionic water soluble polymers of intrinsic viscosity at least 6 dl/g, for instance polymers of acrylamide with acrylic acid containing at least 25% by weight anionic monomer units. The proportion of anionic units may even be as high as 60 or 70% by weight and in some instances even higher.

It may also be desirable to further enhance the efficacy of the composition by including other ingredients. For instance it may be desirable to include a reverse phase anionic or nonionic polyacrylamide into the aqueous composition, such as described in U.S. Pat. No. 5,529,975, incorporated by reference herein. Alternatively an additional ingredient may suitably be a low intrinsic viscosity anionic or nonionic polyacrylamide aqueous polymer, for instance as described in U.S. Pat. No. 5,525,575, incorporated herein by reference. If additional ingredients are included in the aqueous formulation, generally they would be included in an amount of 0.005 to 0.2% by weight of sprayable formulation.

Another aspect of the invention provides a process of applying fertiliser to an area of land or a crop area comprising spraying water to which has been added an aqueous composition comprising water, in solution, a) an inorganic water-soluble compound in an amount of at least 10%, b) an anti-drift agent which is a water soluble anionic polymer of intrinsic viscosity at least 6 dl/g which is formed from water soluble monomer or monomer blend, characterised in that the polymer (b) is present in an amount up to 1.9 wt. % based on weight of composition and wherein the inorganic compound (a) is the fertiliser.

In a preferred aspect of the process for the application of fertiliser, water is pumped through a feed ducting and a mixing zone to a spray manifold supplying one or more spraying devices by which the water is sprayed onto a crop area and the above aqueous composition is metered into the water at or before the mixing zone, In the process of applying a fertiliser the polymer (b) is preferably formed from water soluble monomer or monomer blend of which at least 15% is anionic monomer. The polymer (b) preferably has an intrinsic viscosity of at least 8 dl/g, preferably between 10 and 30 dl/g, especially between 10 and 15 dl/g. The amount of polymer (b) present in the aqueous composition is below 1.9 wt. % based on total weight of composition, preferably below 1.0 wt. %, more preferably below 0.5 wt. %. The process is particularly effective if the amount of polymer (b) present in the aqueous composition is below 0.2 wt. % based on weight of composition, preferably below 0.15 wt. %. The process is more effective if the composition used comprises polymer (b) in an amount between 0.05 wt. % and 0.1 wt. % based on total weight of composition. The preferred types of polymer (b) include polymers formed from water soluble monomer blend comprising of between 20 and 50 wt. % anionic monomer, preferably 25 to 30 wt. %. Particularly preferred polymers for the process are copolymers of acrylamide with acrylic acid, or alkali metal or ammonium salt thereof. In another preferred aspect of the process the aqueous composition is prepared by adding the polymer (b) the form of a powder to the aqueous solution of inorganic water-soluble compound.

In the process of applying a fertiliser the composition should have viscosity which renders the composition easy to handle. It should in particular be easy to handle (ie preferably pumpable, pourable or sprayable) in the equipment which is presently used for spraying. The polymer may be added to the fertiliser at the facility of the fertiliser manufacturer and thus the viscosity should be low enough that the resulting solution can be handled by equipment presently in place in such facilities. Preferably viscosity is below 3,000 cPs, more preferably not more than 1,000 cPs. In particular it is not more than 500 and especially not more than 250 cPs. Particularly preferably it is not more than 100 cPs. Usually it is in the range of 5 to 50 cPs, preferably 10 to 30 cPs, more preferably in the range 15 to 20 cPs. In this specification viscosity is measured using a Brookfield LVT viscometer using spindle 4 at 30 rpm.

A further aspect of the invention relates to a process of applying a herbicide or a pesticide to an area of land or a crop area comprising mixing water, said herbicide or pesticide and a composition comprising water, in solution, a) an inorganic water-soluble compound in an amount of at least 10%, b) an anti-drift agent which is a water soluble anionic polymer of intrinsic viscosity at least 6 dl/g which is formed from water soluble monomer or monomer blend, characterised in that the polymer (b) is present in an amount up to 1.9 wt. % based on weight of composition, and then spraying the mixture.

In a preferred aspect of the process of application of pesticide or herbicide, water is pumped through a feed ducting and a mixing zone to a spray manifold supplying one or more spraying devices by which the water is sprayed onto a crop area and the aqueous composition as defined in claim 1 is metered into the water at or before the mixing zone, wherein the inorganic salt is a fertiliser or herbicide adjuvant.

In the process of applying a pesticide or herbicide the polymer (b) is preferably formed from water soluble monomer or monomer blend of which at least 15% is anionic monomer. The polymer (b) preferably has an intrinsic viscosity of at least 8 dl/g, preferably between 10 and 30 dl/g, especially between 10 and 15 dl/g. The amount of polymer (b) present in the aqueous composition is below 1.9 wt. % based on total weight of composition, preferably below 1.0 wt. %, more preferably below 0.5 wt. %. The process is particularly effective if the amount of polymer (b) present in the aqueous composition is below 0.2 wt. % based on weight of composition, preferably below 0.15 wt. %. The process is more effective if the composition used comprises polymer (b) in an amount between 0.05 wt. % and 0.1 wt. % based on total weight of composition. The preferred types of polymer (b) include polymers formed from water soluble monomer blend comprising of between 20 and 50 wt. % anionic monomer, preferably 25 to 30 wt. %. Particularly preferred polymers for the process are copolymers of acrylamide with acrylic acid, or alkali metal or ammonium salt thereof. In another preferred aspect of the process the aqueous composition is prepared by adding the polymer (b) the form of a powder to the aqueous solution of inorganic water-soluble compound.

Preferably the quantity of herbicide would be in the range 1 to 5 wt. %, more preferably 2 to 3 wt. %, most preferably around 2.5 wt. %. For instance a diluted fertiliser composition to be sprayed contains a systemic herbicide, preferably glyphosate in an amount up to 10 wt. %, preferably 1 to 5 wt. %, more preferably 2 to 3 wt. %, most preferably around 2.5 wt%.

Typically the diluted aqueous fertiliser composition to be sprayed comprises up to 10 wt. % fertiliser and up to 10 wt. % additional agricultural chemical, which is preferably a herbicide or a pesticide, especially a herbicide, such as a systemic herbicide, which is in particular glyphosate.

A preferred diluted aqueous fertiliser composition to be sprayed comprises 1 to 5 wt. % more preferably 2 to 3 wt. %, especially around 2.5 wt. % of the aqueous fertiliser concentrate and 1 to 5 wt. % additional agricultural chemical, which is for instance a herbicide or pesticide, preferably a herbicide, more preferably a systemic herbicide most preferably glyphosate or glufosinate.

One preferred aspect of the invention is a diluted fertiliser composition to be sprayed comprises ammonium sulphate solution concentrate (AMS) in an amount up to 10 wt %, preferably 1 to 5 wt. %, more preferably 2 to 3 wt. %, most preferably around 2.5 wt. % and glyphosate in an amount up to 10 wt. %, preferably 1 to 5 wt. %, more preferably 2 to 4 wt. %, most preferably around 2.5 wt. %. A particularly preferred diluted composition to be sprayed comprises ammonium sulphate solution concentrate (AMS) in an amount up to around 2.5 wt. % and glyphosate in an amount up to around 2.5 wt. %.

A further aspect of the invention relates to a process of applying fertiliser to an area of land comprising spraying water to which has been added an aqueous composition comprising water, in solution, a) an inorganic water-soluble fertiliser in an amount of at least 10%, a water soluble anionic polymer of intrinsic viscosity at least 6 dl/g which is formed from water soluble monomer of monomer blend, characterised in that the polymer (b) is present in an amount up to 1.9 wt. % based on weight of composition. In the process the polymer (b) is preferably formed from water soluble monomer or monomer blend of which at least 15% is anionic monomer, preferably 20 and 50 wt. %, most preferably 25 to 30 wt. %. Furthermore in a more preferred process the polymer (b) desirably has an intrinsic viscosity of at least 8 dl/g, more preferably between 10 and 30 dl/g, especially between 10 and 15 dl/g.

In a particularly preferred the process the polymer (b) is present in an amount below 1.0 wt. % based on total weight of composition, preferably below 0.5 wt. %, even more preferably below 0.2 wt. %, especially below 0.15 wt. % and most preferably in the range 0.1 wt. % to 0.05 wt. %. In a particularly preferred process the polymer (b) is a copolymer of acrylamide with acrylic acid, or alkali metal or ammonium salts thereof, especially a copolymer of acrylamide with sodium acrylate. In a particularly preferred process the fertiliser is ammonium sulphate. In another particularly preferred process the aqueous composition has been formed by adding polymer (b) into water in the form of a powder. In the most preferred process of applying fertiliser a herbicide, preferably a systemic herbicide, especially glyphosate is combined with the water which is sprayed. Thus the invention also relates to a method of improving the spray drift properties of a fertiliser composition by combining up to 1.9 wt. %, by weight of composition, of a water soluble anionic polymer of intrinsic viscosity at least 6 dl/g, formed from water soluble anionic monomer or monomer blend.

In the process of applying a herbicide or pesticide the composition should have viscosity which renders it easy to handle. It should in particular be easy to handle (ie preferably pumpable, pourable or sprayable) in the equipment which is presently used for spraying. The polymer may be added to the inorganic water-soluble compound at the facility of the manufacturer of the inorganic compound, for example a fertiliser manufacturer, and thus the viscosity should be low enough that the resulting solution can be handled by equipment presently in place in such facilities. Preferably viscosity is below 3,000 cPs, more preferably not more than 1,000 cPs. In particular it is not more than 500 and especially not more than 250 cPs. Particularly preferably it is not more than 100 cPs. Usually it is in the range of 5 to 50 cPs, preferably 10 to 30 cPs, more preferably in the range 15 to 20 cPs. In this specification viscosity is measured using a Brookfield LVT viscometer using spindle 4 at 30 rpm.

The invention further relates to a method of improving the spray drift properties during the spraying of a pesticide or herbicide composition by the application of a composition comprising water, in solution, a) an inorganic water-soluble compound in an amount of at least 10% by weight, b) an anti-drift agent which is a water soluble anionic polymer of intrinsic viscosity at least 6 dl/g which is formed from water soluble monomer or monomer blend, characterised in that the water-soluble polymer (b) is present in an amount up to 1.9 wt. % based on weight of composition.

Preferably the inorganic water-soluble compound (a) is a fertiliser or herbicide adjuvant.

In the method of improving the spray drift properties during the spraying of a pesticide or herbicide composition the polymer (b) is preferably formed from water soluble monomer or monomer blend of which at least 15% is anionic monomer. The polymer (b) preferably has an intrinsic viscosity of at least 8 dl/g, preferably between 10 and 30 dl/g, especially between 10 and 15 dl/g. The amount of polymer (b) present in the aqueous composition is below 1.0 wt. % based on total weight of composition, preferably below 0.5 wt. %. The method is particularly effective if the amount of polymer (b) present in the aqueous composition is below 0.2 wt. % based on weight of composition, preferably below 0.15 wt. %. The method is more effective if the composition used comprises polymer (b) in an amount between 0.05 wt. % and 0.1 wt. % based on total weight of composition. The preferred types of polymer (b) include polymers formed from water soluble monomer blend comprising of between 20 and 50 wt. % anionic monomer, preferably 25 to 30 wt. %. Particularly preferred polymers for the process are copolymers of acrylamide with acrylic acid, or alkali metal or ammonium salt thereof. In another preferred aspect of the method the aqueous composition is prepared by adding the polymer (b) the form of a powder to the aqueous solution of inorganic water-soluble compound.

The invention relates to a method of improving the spray drift properties during the spraying of a fertiliser by providing an aqueous composition comprising water, in solution, a) an inorganic water-soluble compound in an amount of at least 10% by weight, b) an anti-drift agent which is a water soluble anionic polymer of intrinsic viscosity at least 6 dl/g which is formed from water soluble monomer or monomer blend, characterised in that the water-soluble polymer (b) is present in an amount up to 1.9 wt. % based on weight of composition and wherein the inorganic water soluble compound is the fertiliser.

In the method of improving the spray drift properties during the spraying of a fertiliser the polymer (b) is preferably formed from water soluble monomer or monomer blend of which at least 15% is anionic monomer. The polymer (b) preferably has an intrinsic viscosity of at least 8 dl/g, preferably between 10 and 30 dl/g, especially 10 and 15 dl/g. The amount of polymer (b) present in the aqueous composition is below 1.0 wt. % based on total weight of composition, preferably below 0.5 wt. %. The method is particularly effective if the amount of polymer (b) present in the aqueous composition is below 0.2 wt. % based on weight of composition, preferably below 0.15 wt. %. The method is more effective if the composition used comprises polymer (b) in an amount between 0.05 wt. % and 0.1 wt. % based on total weight of composition. The preferred types of polymer (b) include polymers formed from water soluble monomer blend comprising of between 20 and 50 wt. % anionic monomer, preferably 25 to 30 wt. %. Particularly preferred polymers for the process are copolymers of acrylamide with acrylic acid, or alkali metal or ammonium salt thereof. In another preferred aspect of the process the aqueous composition is prepared by adding the polymer (b) the form of a powder to the aqueous solution of inorganic water-soluble compound.

The following examples illustrate the invention.

EXAMPLE 1

A range of Sodium acrylate/acrylamide copolymers with a range of IVs and anionicities is assessed for solubility at 0.1% w/w concentration in 32% ammonium sulphate solution. In each test the polymer in powder form is mixed with ammonium sulphate solution in a glass jar and then tumbled for several hours. The results are shown in Table 1

TABLE 1

| Polymer | Anionic content (wt. %) | IV | Solubilty |
| --- | --- | --- | --- |
| A | 28 | 11.5 | Soluble |
| B | 48 | 23.2 | Soluble |
| C | 47 | 11.6 | Soluble |
| D | 47 | 14.4 | Soluble |
| E | 84 | 12.2 | Soluble |
| F | 95.5 | 11.0 | Soluble |
| G | 100 | 13.7 | Soluble |

EXAMPLE 2

A range of sodium acrylate / acrylamide copolymers with a range of IVs and anionicities are assessed for anti-drift properties. For each test each polymer is added at different concentrations to a 32% ammonium sulphate solution and tumbled until the polymer has dissolved to form an aqueous concentrate. In each case 2.5 ml of concentrate is mixed with 95 ml water and 2.5 ml of a commercially available glyphosate formulation containing 480 g/l isopropylamine salt of glyphosate to form a diluted composition ready for spraying. The diluted composition is sprayed through a 110° flat fan nozzle at a pressure of 3 bar and a height of 15 cm above an absorbent bed. The reduction of the spray angle over an equivalent composition in the absence of polymer is measured. The increase in spray angle reduction is measured as the polymer dose is doubled. The results are shown in Table 2.

Adequate spray drift control is determined by a reduction of at least 3%, preferably between 4 and 15 %, most preferably in the range of 5 to 10%.

EXAMPLE 3

Samples of aqueous fertiliser concentrate comprising either an anionic or a cationic polymer are assessed for storage stability over 2 days. Cationic polymers are acrylamide copolymers with dimethylaminoethyl acrylate, methyl chloride quaternary salt. Anionic polymers are acrylamide copolymers with sodium acrylate. The results are shown in Table 3.

TABLE 2

| Polymer | Anionic Content (wt. %) | IV | Concentration of polymer in aqueous Concentrate (wt. %) | Spray Angle Reduction (%) | % Increase in Spray Angle Reduction as Concentration is doubled |
|---|---|---|---|---|---|
| A | 28 | 11.5 | 0.05 | 5.1 | 4.4 |
| | | | 0.10 | 9.5 | |
| | | | 0.15 | 14.0 | |
| B | 48 | 23.2 | 0.05 | 5.5 | 7.2 |
| | | | 0.10 | 12.7 | |
| | | | 0.15 | 28.0 | |
| C | 47 | 11.6 | 0.10 | 8.8 | 3.6 |
| | | | 0.20 | 12.4 | |
| D | 47 | 14.4 | 0.10 | 8.8 | 9.4 |
| | | | 0.15 | 12.4 | |
| | | | 0.20 | 18.2 | |
| E | 84 | 12.2 | 0.10 | 4.5 | 16.3 |
| | | | 0.15 | 11.3 | |
| | | | 0.20 | 20.8 | |
| F | 95.5 | 11.0 | 0.10 | 5.6 | 16.9 |
| | | | 0.15 | 7.5 | |
| | | | 0.20 | 22.5 | |
| G | 100 | 13.7 | 0.10 | 5.3 | 19.9 |
| | | | 0.15 | 13.1 | |
| | | | 0.20 | 25.2 | |

TABLE 3

| Polymer | % Ionic | Polymer Concentration (%) | Stability over 2 days |
|---|---|---|---|
| H | 73% cationic | 1 | gelatinous mass formed |
| | | 1.5 | gelatinous mass formed |
| | | 2 | gelatinous mass formed |
| I | 76% cationic | 1 | gelatinous mass formed |
| | | 2 | gelatinous mass formed |

TABLE 3-continued

| Polymer | % Ionic | Polymer Concentration (%) | Stability over 2 days |
|---|---|---|---|
| J | 65% anionic | 2 | stable |
| | | 5 | stable |
| | | 10 | stable |
| K | 95.5% anionic | 1 | stable |
| L | 67% anionic | 1 | stable |

EXAMPLE 4

Winter barley plants were sown in peat trays under growing room conditions. At the ⅔ leaf growth stage, the plants were sprayed with a range of treatments (detailed below) using a compressed air stationary sprayer. The volume of water used was equivalent to 250 litres per hectare at a pressure of 3 bar, through a Lurmark 015 F80° flat fan nozzle.

Treatments

1. Cipac D water—control.
2. Glyphosate.
3. Glyphosate+Ammonium sulphate (34%).
4. Glyphosate+Ammonium sulphate(10%).
5. Glyphostae+Ammonium sulphate(34%)/Polymer X (Copolymer of acrylamide/acrylic acid (4.5/95.5 wt./wt.) (0.1% by weight of formulation).
6. Glyphosate+Ammonium sulphate (10%)/Polymer Y (Copolymer of acrylamide/acrylic acid (72/28 wt./wt/) (1.0% of formulation).

The glyphosate used was a proprietary glyphosate formulation containing 480 g/l isopropylamine salt of glyphosate, equivalent to 360 g/l glyphosate. The level of Glyphosate used was equivalent to 1.0 litre per hectare. The ammonium sulphate (AMS) Polymer X formulation was used at a rate equivalent to 9.38 litres per hectare, and the AMS/Polymer Y formulation used at a rate equivalent to 1.88 litres per hectare. Treatment (3) was used at the same dose rate as treatment (5) i.e. equivalent to 9.38 litres per hectare, and treatment (4) was used at the same dose rate as treatment (6) i.e. equivalent to 1.88 litres per hectare.

Cipac D water (containing 342 ppm Ca as calcium carbonate) was used throughout the trial and each treatment was replicated four times.

Three days after application of treatments, the plants were cut just above the growing point. The percentage re-growth was assessed 9 days after the application. The percent kill assessment was made 21 days after the application of treatments.

The percentage re-growth and percentage kill of the plants for each of the treatments are given in Table 4.

TABLE 4

| | 1 Control | 2 Glyphosate | 3 Glyphosate + AMS 34% | 4 Glyphosate + AMS 10% | 5 Glyphosate + AMS 34% + Polymer X | 6 Glyphosate + AMS 10% + Polymer Y |
|---|---|---|---|---|---|---|
| Re-growth after 9 days (%) | 99 | 105 | 10 | 19 | 6 | 15 |

TABLE 4-continued

| | 1<br>Con-<br>trol | 2<br>Glypho-<br>sate | 3<br>Glypho-<br>sate +<br>AMS<br>34% | 4<br>Glypho-<br>sate +<br>AMS<br>10% | 5<br>Glyphosate +<br>AMS 34% +<br>Polymer X | 6<br>Glyphosate +<br>AMS 10% +<br>Polymer Y |
|---|---|---|---|---|---|---|
| Kill after 21 days (%) | 5 | 7 | 68 | 43 | 76 | 51 |

As can be seen from the results the polymers clearly enhance the efficacy of the Glyphosate formulation above that of the AMS formulations alone.

What is claimed is:

1. A process of applying a herbicide or a pesticide to an area of land or a crop area comprising mixing water, said herbicide or pesticide and a composition comprising water, in solution, a) an inorganic water-soluble compound in an amount of at least 10% by weight, b) an anti-drift agent which is a water soluble anionic polymer of intrinsic viscosity at least 6 dl/g which is formed from water soluble monomer or monomer blend, characterised in that the polymer (b) is present in an amount up to 1.9 wt. % based on weight of composition and then spraying the mixture.

2. A process according to claim 1 in which water is pumped through a feed ducting and a mixing zone to a spray manifold supplying one or more spraying devices by which the water is sprayed onto an area of land or a crop area and an aqueous composition comprising water, in solution, a) an inorganic water-soluble compound in an amount of at least 10% by weight, b) an anti-drift agent which is a water-soluble anionic polymer of intrinsic viscosity at least 6 dl/g which is formed from water soluble monomer or monomer blend, characterized in that the polymer (b) is present in an amount up to 1.9 wt. % based on the weight of the composition is metered into the water at or before the mixing zone, wherein the inorganic water-soluble compound (a) is either a fertilizer or herbicide adjuvant and is selected from the group consisting of ammonium nitrate, ammonium sulphate, mono ammonium phosphate, diammonium phosphate, mono potassium phosphate, dipotassium phosphate, polyphosphate salts, potassium chloride, potassium sulphate and calcium nitrate.

3. A process according to claim 1 in which the polymer (b) is formed from water soluble monomer or monomer blend of which at least 15% is anionic monomer.

4. A process according to claim 1 in which the polymer (b) has an intrinsic viscosity of at least 8 dl/g.

5. A process according to claim 1 in which the polymer (b) is present in an amount below 1.0 wt. % based on total weight of composition.

6. A process according to claim 1 in which the polymer (b) is present in an amount below 0.2 wt. % based on weight of composition.

7. A process according to claim 1 in which the polymer (b) is present in an amount between 0.1 wt. % and 0.05 wt. % based on total weight of composition.

8. A process according to claim 1 in which the polymer (b) is formed from water soluble monomer or monomer blend comprising of between 20 and 100 wt. %, anionic monomer based on total weight of polymer.

9. A process according to claim 1 in which the inorganic water-soluble compound is either a fertilizer or herbicide adjuvant and is selected from the group consisting of ammonium nitrate, ammonium sulphate, mono ammonium phosphate, diammonium phosphate, mono potassium phosphate, dipotassium phosphate, polyphosphate salts, potassium chloride, potassium sulphate and calcium nitrate.

10. A process according to claim 1 in which the inorganic water-soluble compound is ammonium sulphate.

11. A process according to claim 1 in which the polymer (b) is a copolymer of acrylamide with acrylic acid, or alkali metal or ammonium salt thereof.

12. A process according to claim 1 that improves spray drift properties during the spraying of a pesticide or glyphosate by the application of a composition comprising water, in solution, a) an inorganic water-soluble compound in an amount of at least 10% by weight, b) an anti-drift agent which is a water soluble anionic polymer of intrinsic viscosity at least 6 dl/g which is formed from water soluble monomer or monomer blend, characterised in that the polymer (b) is present in an amount up to 1.9 wt. % based on weight of composition to said pesticide or herbicide prior to spraying.

13. A process for the preparation of the composition comprising water, in solution, a) an inorganic water-soluble compound in an amount of at least 10% by weight, b) an anti-drift agent which is a water soluble anionic polymer of intrinsic viscosity at least 6 dl/g which is formed from water soluble monomer or monomer blend, characterised in that the polymer (b) is present in an amount up to 1.9 wt. % based on weight of composition in which the polymer (b) is added in the form of a powder to an aqueous solution comprising at least 10 wt. % wherein the inorganic water-soluble compound (a) is either a fertilizer or herbicide adjuvant and is selected from the group consisting of ammonium nitrate, ammonium sulphate, mono ammonium phosphate, diammonium phosphate, mono potassium phosphate, dipotassium phosphate, polyphosphate salts, potassium chloride, potassium sulphate and calcium nitrate.

* * * * *

UNITED STATES PATENT AND TRADEMARK OFFICE
CERTIFICATE OF CORRECTION

PATENT NO.   : 6,288,010 B1
DATED        : September 11, 2001
INVENTOR(S)  : Simon Alexander Hanson Rose et al., It is certified that error appears in the above-identified patent and that said Letters Patent is hereby corrected as shown below:

<u>Title page,</u>
Item [30], Foreign Application Priority Data, should read:

-- Oct. 30, 1998   (GB) ...............................9823752 --.

Signed and Sealed this

Eighteenth Day of March, 2003

JAMES E. ROGAN
*Director of the United States Patent and Trademark Office*